United States Patent [19]
Ken et al.

[11] Patent Number: 5,833,705
[45] Date of Patent: *Nov. 10, 1998

[54] STRETCH RESISTANT VASO-OCCLUSIVE COILS

[75] Inventors: Christopher G. M. Ken, San Mateo; Son M. Gia, San Jose; Erik T. Engelson, Menlo Park, all of Calif.

[73] Assignee: Target Therapeutics, Inc., Fremont, Calif.

[*] Notice: The term of this patent shall not extend beyond the expiration date of Pat. No. 5,582,619.

[21] Appl. No.: 717,285

[22] Filed: Sep. 20, 1996

Related U.S. Application Data

[63] Continuation-in-part of Ser. No. 497,331, Jun. 30, 1995, Pat. No. 5,582,619, and Ser. No. 607,593, Feb. 27, 1996, abandoned.

[51] Int. Cl.$^6$ .................................................. A61M 29/00
[52] U.S. Cl. .............................. 606/191; 606/198; 623/1
[58] Field of Search .................................... 606/191, 198, 606/194, 151, 213, 200

[56] References Cited

U.S. PATENT DOCUMENTS

| | | |
|---|---|---|
| 3,174,851 | 3/1965 | Buehler et al. |
| 3,351,463 | 11/1967 | Rozner et al. |
| 3,753,700 | 8/1973 | Harrison et al. |
| 4,994,069 | 2/1991 | Ritchart et al. |
| 5,108,407 | 4/1992 | Geremia et al. |
| 5,122,136 | 6/1992 | Guglielmi et al. |
| 5,180,366 | 1/1993 | Woods .................................. 606/194 |
| 5,217,484 | 6/1993 | Marks . |
| 5,226,911 | 7/1993 | Chee et al. |
| 5,234,437 | 8/1993 | Septeka . |
| 5,250,071 | 10/1993 | Palermo . |
| 5,261,916 | 11/1993 | Engelson . |
| 5,304,194 | 4/1994 | Chee et al. |
| 5,304,195 | 4/1994 | Twyford, Jr. et al. |
| 5,312,415 | 5/1994 | Palermo . |
| 5,329,942 | 7/1994 | Gunther et al. ........................ 606/200 |
| 5,350,397 | 9/1994 | Palermo et al. |
| 5,354,295 | 10/1994 | Guglielmi et al. |
| 5,365,942 | 11/1994 | Shank . |
| 5,382,259 | 1/1995 | Phelps et al. |
| 5,382,260 | 1/1995 | Dormandy, Jr. et al. |
| 5,387,219 | 2/1995 | Rappe . |
| 5,441,516 | 8/1995 | Wong et al. ........................... 606/200 |
| 5,645,558 | 7/1997 | Horton . |

FOREIGN PATENT DOCUMENTS 754435  1/1997  European Pat. Off. .

*Primary Examiner*—Michael Powell Buiz
*Assistant Examiner*—Kevin Truong
*Attorney, Agent, or Firm*—Morrison & Foerster LLP

[57] ABSTRACT

This is an implantable vaso-occlusive device. It is typically a vaso-occlusive coil comprised of a primary helically wound coil which may then be wound into a secondary shape. Central to the invention is the use of a stretch-resisting member fixedly attached within at least a portion of the primary coil. The stretch-resisting member may be formed into coil tips at the ends of the coil by melting the polymeric fibers or alloys or by attaching the fibers with a glue. This stretch-resisting member is for the primary purpose of preventing stretching of the coil during movement of that coil, e.g., by retrieval or repositioning after deployment. The device typically has a self-forming secondary shape made from a pre-formed primary linear helically wound coil, although it need not have the secondary form. External fibers may be attached to the device and affixed to the pre-formed linear member to increase. The vaso-occlusive member may be also be covered with a fibrous braid. The device is typically introduced into the body through a catheter. The device is passed axially through the catheter sheath and assumes its secondary form upon exiting the catheter.

24 Claims, 7 Drawing Sheets

STRETCH RESISTANT VASO-OCCLUSIVE COILS

RELATED APPLICATIONS

This patent application is a continuation-in-part of U.S. Pat. application Ser. No. 08/497,331 filed Jun. 30, 1995 now U.S. Pat. No. 5,582,619 and U.S. Pat. application Ser. No. 08/607,593 filed Feb. 27, 1996, now abandoned.

FIELD OF THE INVENTION

This invention is an implantable vaso-occlusive device. It is typically a vaso-occlusive coil comprised of a primary helically wound coil which may then be wound into a secondary shape. Central to the invention is the use of a stretch-resisting member extending through the lumen formed is fixedly attached to the coil in at least two locations. The stretch-resisting member may be formed into coil tips at the ends of the coil using simple equipment such as soldering irons or the like. The tips are typically of the same diameter as is the coil body itself. This stretch-resisting member is for the primary purpose of preventing stretching of the coil during movement of that coil, e.g., by retrieval or repositioning after deployment. The device typically has a self-forming secondary shape made from a pre-formed primary linear helically wound coil, although it need not have the secondary form. External fibers may be attached to the device and affixed to the pre-formed linear member to increase thrombogenicity. The vaso-occlusive member may be also be covered with a fibrous braid. The device is typically introduced into the body through a catheter. The device is passed axially through the catheter sheath and assumes its secondary form upon exiting the catheter.

BACKGROUND OF THE INVENTION

Vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings which may be dimensioned to engage the walls of the vessels. Other less stiff, helically coiled devices have been described, as well as those involving woven braids.

For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration —which is better suited to occlude the vessel —once the device is so placed. Ritchart et al. describes a variety of shapes. The secondary shapes of the disclosed coils include "flower" shapes and double vortices. A random secondary shape is described, as well.

Vaso-occlusive coils having attached fibrous elements in a variety of secondary shapes are shown in U.S. Pat. No. 5,304,194, to Chee et al. Chee et al. describes a helically wound device having a secondary shape in which the fibrous elements extend in a sinusoidal fashion down the length of the coil. These coils, as with Ritchart et al., are produced in such a way that they will pass through the lumen of a catheter in a generally straight configuration and, when released from the catheter, form a relaxed or folded shape in the lumen or cavity chosen within the human body. The fibrous elements shown in Chee et al. enhance the ability of the coil to fill space within the vasculature and to facilitate formation of embolus and subsequent allied tissue.

There are a variety of ways of discharging shaped coils and linear coils into the human vasculature. In addition to those patents which apparently describe only the physical pushing of a coil out into the vasculature (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

Vaso-occlusive coils having little or no inherent secondary shape have also been described. For instance, in U.S. Pat. application Ser. No. 07/978,320, filed Nov. 18, 1992, entitled "Ultrasoft Embolization Coils with Fluid-Like Properties" by Berenstein et al., is found a coil having little or no shape after introduction into the vascular space.

None of these devices are helical coils which contain a stretch-resisting member contained therein.

SUMMARY OF THE INVENTION

This invention is a vaso-occlusive device comprising a helically wound coil which is formed by winding a wire into a first or primary helix to form an outer helical member having first and second ends. A stretch resistant member extending through the lumen formed is fixedly attached to the coil in at least two locations.

The primary helix, with its included stretch-resistant member, may be wound into a secondary form and heat-treated to preserve that form, desirably prior to the step of including the stretch-resisting member into the coil. The secondary form may be one which, when ejected from a delivery catheter, forms a specific shape. Such a shape might, e.g., fill a vascular cavity such as an aneurysm, or perhaps, a fistula. The stiffness of the various parts of the coil may be tailored to enhance the utility of the device for specific applications. Fibrous materials may be woven into the member or tied or wrapped onto it.

The device is used simply by temporarily straightening the device and introducing it into a suitable catheter, the catheter already having been situated so that its distal opening is at the selected site in the body. The device is then pushed through the catheter and, upon its ejection from the distal end of the catheter into the vascular cavity, assumes its relaxed or secondary shape.

The device is typically used in the human vasculature to form emboli but may be used at any site in the human body where an occlusion such as one produced by the inventive device is needed.

DESCRIPTION OF THE INVENTION

Figure 1A:
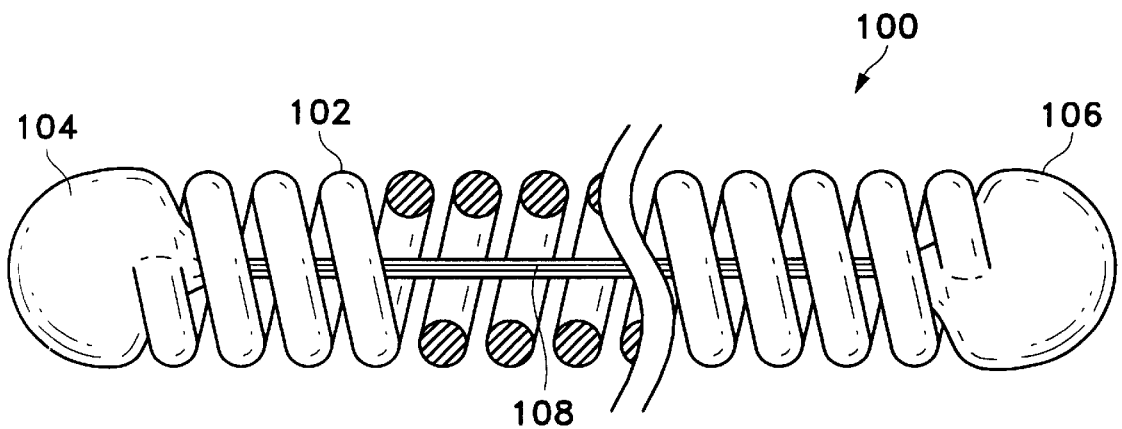
FIG. 1A shows a side view, partial cutaway of a vaso-occlusive coil made according to the invention having a generally linear fibrous stretch-resisting member.
Figure 1B:
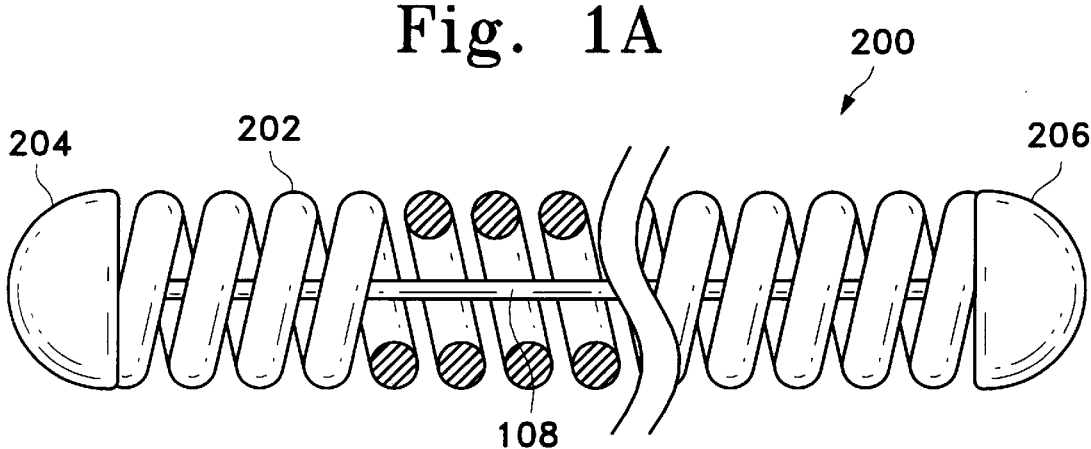
FIG. 1B shows a side view, partial cutaway of a vaso-occlusive coil made according to the invention having a generally linear wire stretch-resisting member.
Figure 1C:
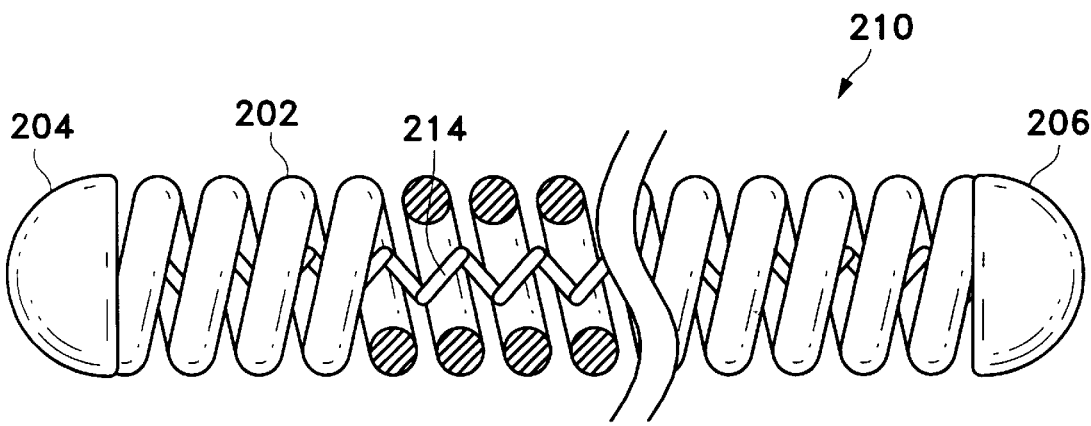
FIG. 1C shows a side view, partial cutaway of a vaso-occlusive coil made according to the invention having a generally helical stretch-resisting member.

FIGS. 1A, 1B, and 1C show side-view partial cross-sections (or cutaways) of highly desirable variations of the inventive coil (100, 200, 210).

The variations shown in FIGS. 1A and 1B are made up of a helically wound outer coil (102, 202) having a first end (104, 204) and a second end (106, 206). We refer to this form as the as the "primary" winding or shape. These variations include a stretch-resisting member (108, 208, 214) which is shown to be fixedly attached both to the first end (104, 204) and to the second end (106, 206). In certain circumstances, it may be desirable to attach the stretch-resisting member (108, 208) only to one of the two ends, to at least one site between the to ends, or to neither of the two ends. Clearly, for attaining stretch resistance, the stretch resisting member must be attached to at least two points on the coil.

The stretch-resisting member (108) of the variation shown in FIG. 1A is fibrous and desirably polymeric. It may be a thermoplastic or thermosetting and comprise a bundle of threads or a single filament melted onto, glued, or otherwise fixedly attached to the vaso-occlusive coil (100). In some instances, it may also be desirable to include one or more metallic strands in the stretch-resisting member (108) to provide stiffness or electrical conductance for specific applications.

The stretch-resisting member (208) of the variation shown in FIG. 1B is a simple wire or "ribbon" which is soldered, brazed, glued, or otherwise fixedly attached to the first end (204), second end (206), or to the coil at one or more locations intermediate to those the ends.

The variation shown in FIG. 1C includes a stretch-resisting member (214) which is comprised of a helically wound coil which is soldered, brazed, glued, or otherwise fixedly attached to the first end (204) or second end (206) or in one or more intermediate locations. The stretch-resisting member (214) in this configuration provides a greater measure of lateral flexibility than the wire variation (208 in FIG. 1B). It may be wound in either the same direction as is the outer coil (202) or in the alternate direction. A modest drawback to this variation is that it will stretch more than the FIG. 1B variation when axially stressed.

The materials used in constructing the vaso-occlusive coil (102, 202) and the stretch resisting member (108, 208, 214) may be any of a wide variety of materials; preferably, a radio-opaque material such as a metal or a polymer is used. Suitable metals and alloys for the wire making up the primary coil (102, 202) and the stretch-resisting member (108, 208, 214) include the Platinum Group metals, especially platinum, rhodium, palladium, rhenium, as well as tungsten, gold, silver, tantalum, and alloys of these metals. These metals have significant radio-opacity and in their alloys may be tailored to accomplish an appropriate blend of flexibility and stiffness. They are also largely biologically inert. Highly preferred is a platinum/tungsten alloy, e.g., 8% tungsten and the remainder platinum.

The ribbon or coil stretch-resisting members (208, 214) may also be of any of a wide variety of stainless steels if some sacrifice of radio-opacity and flexibility may be tolerated. Very desirable materials of construction, from a mechanical point of view, are materials which maintain their shape despite being subjected to high stress. Certain "super-elastic alloys" include various nickel/titanium alloys (48–58 atomic % nickel and optionally containing modest amounts of iron); copper/zinc alloys (38–42 weight % zinc); copper/zinc alloys containing 1–10 weight % of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as very small diameter wire.

If a superelastic alloy such as nitinol is used in the device, the diameter of the coil wire may be significantly smaller than that used when the relatively more ductile platinum or platinum/tungsten alloy is used as the material of construction.

The coils may be made of radiolucent fibers or polymers (or metallic threads coated with radiolucent or radio-opaque fibers) such as Dacron (polyester), polyglycolic acid, polylactic acid, fluoropolymers (polytetrafluoroethylene), Nylon (polyamide), or even silk. Should a polymer be used as the major component of the vaso-occlusive coil member, it is desirably filled with some amount of a radio-opaque material such as powdered tantalum, powdered tungsten, bismuth oxide, barium sulfate, and the like.

The coil material is first wound into a primary coil (102, 202). The primary coil is typically linear after it has been wound. Generally speaking, when the coil (102, 202) is a metallic coil and that coil is a platinum alloy or a super-elastic alloy such as nitinol, the diameter of the wire used in the production of the coil (102, 202) will be in the range of 0.00025 and 0.006 inches. The wire is wound into a primary coil (102, 202) having a primary diameter of between 0.003 and 0.025 inches. For most neurovascular indications, the preferable primary coil (102, 202) diameter is 0.008 to 0.018 inches. We have generally found that the coil wire may be of sufficient diameter to provide a hoop strength to the resulting device sufficient to hold the device in place within the chosen body site, lumen or cavity, without substantially distending the wall of the site and without moving from the site as a result of the repetitive fluid pulsing found in the vascular system.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Once the primary coil (102, 202) is wound, the stretch-resisting member (108, 208) is inserted into the lumen of the primary coil (102, 202) and secured to the coil as desired. Ends (104, 204, 106, 206) are preferably of the same diameter as is the primary coil (102, 202).

Suitable polymeric materials for the polymeric stretch-resisting member (108) can be either thermosetting or thermoplastic. Thermoplastics are preferred because they allow simplification of the procedure for constructing the device (100) since they may be melted and formed into the end or ends (104, 106). Simple devices such as soldering irons may be used to form the ends. Thermosetting plastics would typically be held in place by an adhesive. Suitable polymers include most biocompatible materials which may be made into fibers but include polyester such as polyethyleneterephthalate (especially Dacron) and polyamides including the Nylons, polyglycolic acid, polylactic acid, fluoropolymers (polytetrafluoro-ethylene), or even silk. Especially preferred because of the long history of safe and effective usage in the human body is fibrous polyethyleneterephthalate (PET) sold as Dacron.

Figure 2A:
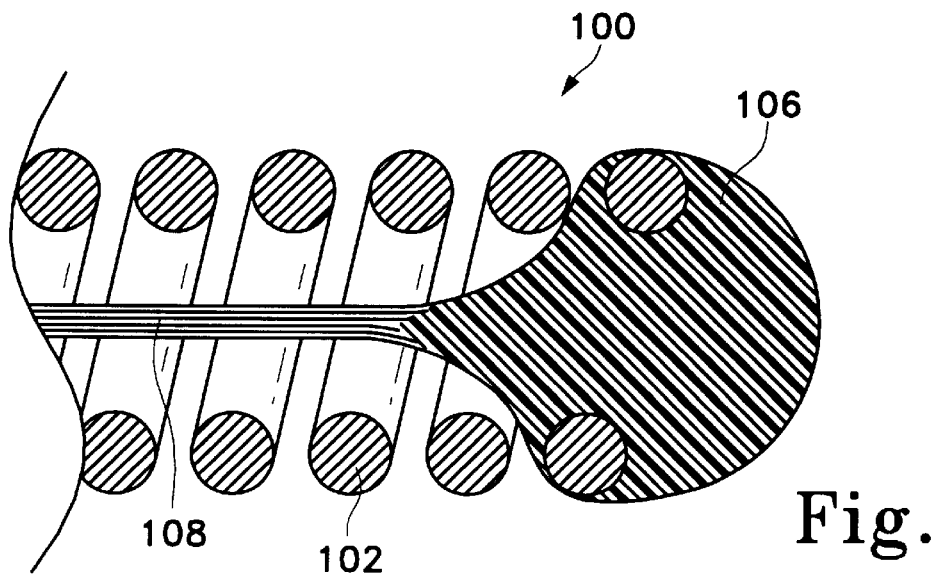
FIGS. 2A, 2B, and 2C show side view, partial cutaways of typical ends of the inventive vaso-occlusive coils.

FIG. 2A shows a side-view partial cross-section of one end of inventive coil (100). FIG. 2A also shows the helically wound outer coil (102) having an end (106) which is formed from a formerly molten fiber which also makes up the stretch-resisting member (114). An end of this type may be considered to have modestly higher vaso-occluding properties than a metallic end. Other functional equivalents to this structure include ends (106) formed of glues such as epoxies and their equivalents, and which are mechanical in nature.

Figure 2B:
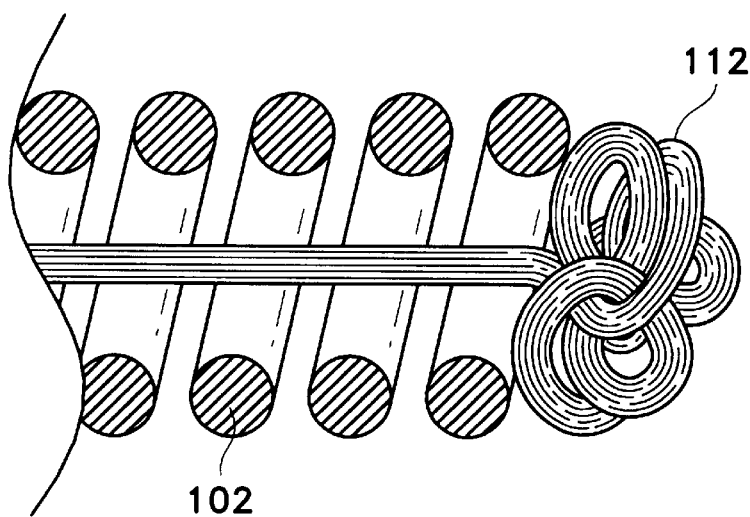
Figure 2C:
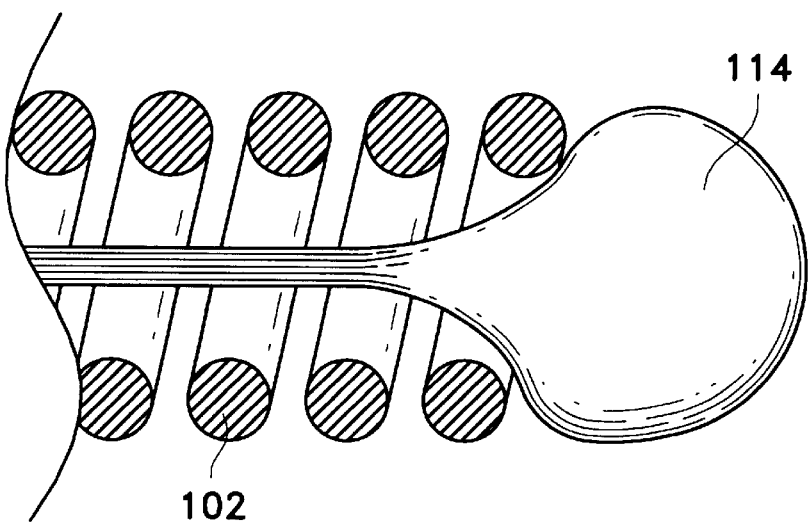

FIG. 2B shows an external knot (112) which fixes the length of the coil member (102) and keeps it from stretching; FIG. 2C shows a reformed mass of formerly molten polymer or of glue which is of a diameter larger than the inner diameter of coil (102) and prevents the coil from stretching. The knot (112) and block (114) are not shown to be attached to the coil (102) but may be.

The variations shown in FIGS. 1A, 1B, 1C and 2A, 2B, and 2C are designed to be deployed by use of a pusher and a catheter in the manner discussed in Ritchart et al, discussed above. Other methods (and concomitant fixtures or joints to accomplish those methods) may also be used.

Figure 3A:
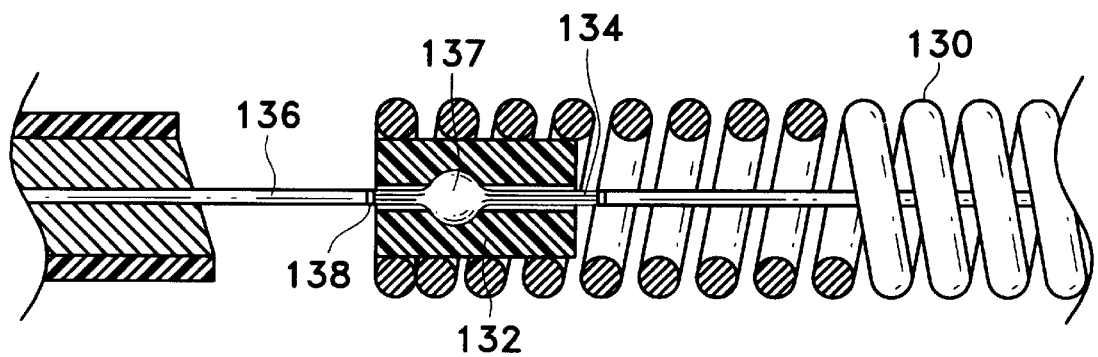
FIGS. 3A and 3B show a side view, partial cutaways of electrolytically severable joints in combination with a vaso-occlusive coil made according to the invention.
Figure 3B:
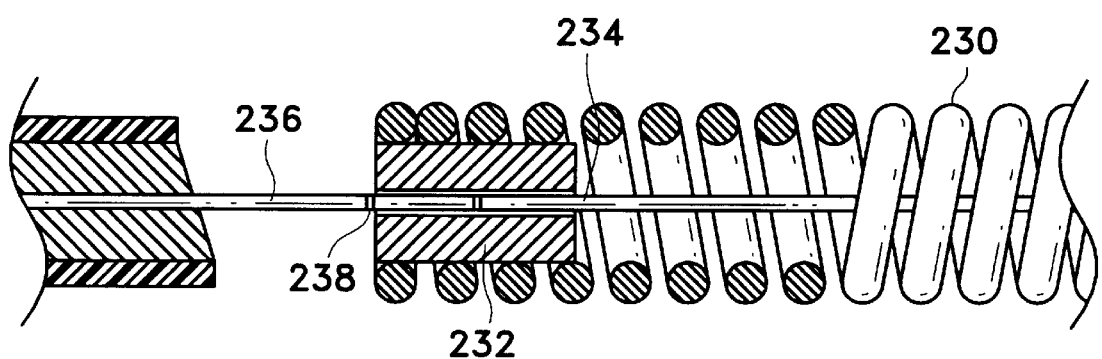

For instance, the end of the device may be adapted to accept an electrolytically severable joint of the type discussed in U.S. Pat. No. 5,354,295 and its parent, U.S. Pat. No. 5,122,136, both to Guglielmi and Sepetka, described above. FIGS. 3A and 3B depict, in partial cross section, such variations. The vaso-occlusive coil (130, 230) is attached to a fill member (132, 232). The fill member (132, 232) preferably comprises a thermoplastic formed into place or an epoxy or the like and adheres, in turn, both to the stretch resistant member (134, 234) and the core wire (136, 236). The core wire (136, 236) in this variation has an enlarged member which is embedded in the fill member (132, 232). The core wire (136, 236) is insulated, typically with a combination of polytetrafluoroethylene and parylene (polyparaxyxylene), except for a small sacrificial joint (138, 238) which is intended to be the site of the electrolysis as the joint (138, 238) is eroded or severed and the coil deployed into the body site. The details of this variation (sans stretch-resistant member (136, 236)) are discussed in Gia et al, U.S. Pat. application Ser. No. 08/367,061, filed Dec. 30, 1994, the entirety of which is incorporated by reference.

Figure 4A:
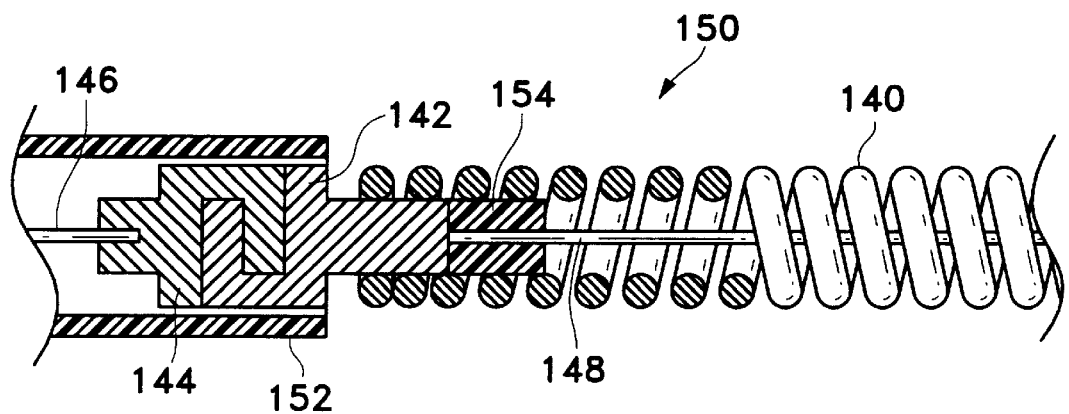
FIGS. 4A and 4B show a side view, partial cutaway of a typical mechanically detachable joint in combination with a vaso-occlusive coil made according to the invention.
Figure 4B:
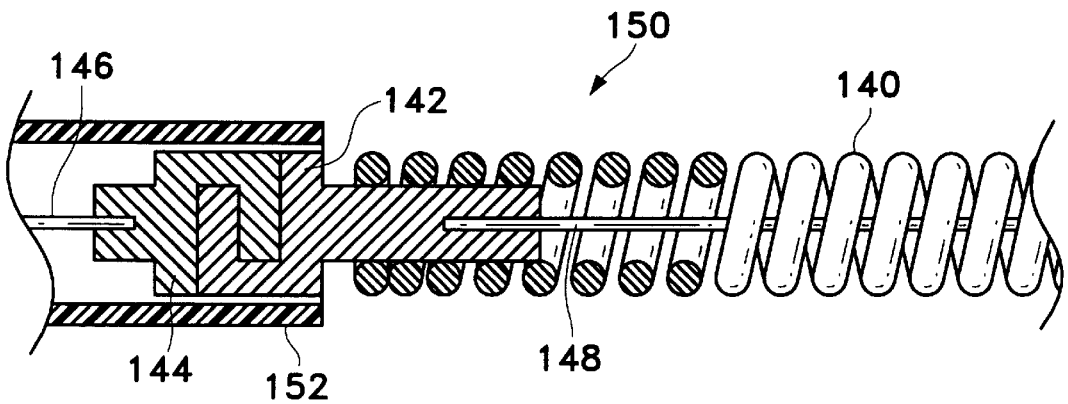

FIG. 4A shows still another variation of a joint for releasing the inventive coil into a site within the human body. In this instance, the joint is mechanically deployed. The primary coil (140) incorporates interlocking clasps, one (142) located on an end of the coil (140) and one (144) located on the end of a pusher (146). The stretch-resisting member (148) is attached to the interlocking clasp (142) via a filler block (154). Again, the filler block (154) comprises a material (e.g., a thermoplastic or adhesive material) which may be placed in the coil and will adhere to the stretch-resistant member (148). The coil assembly (150), made up of the primary coil (140), interlocking clasp (142), and stretch-resisting member (148) is deployed by retracting catheter body (or sheath) (152). FIG. 4B shows a variation of the device depicted in FIG. 4A which does not employ special filler block material (154) for adhering to the stretch-resistant member.

Other mechanically deployable joints suitable for use with the inventive coil are described in:

U.S. Pat. No. 5,234,437, to Sepetka, (shows a method of unscrewing a helically wound coil from a pusher having interlocking surfaces).

U.S. Pat. No. 5,250,071, to Palermo, (shows an embolic coil assembly using interlocking clasps mounted both on the pusher and on the embolic coil)

U.S. Pat. No. 5,261,916, to Engelson, (shows a detachable pusher/vaso-occlusive coil assembly having an interlocking ball and keyway-type coupling)

U.S. Pat. No. 5,304,195, to Twyford et al. (shows a pusher-vaso-occlusive coil assembly having an affixed, proximally extending wire carrying a ball on its proximal end and a pusher having a similar end, which two ends are interlocked and disengage when expelled from the distal tip of the catheter)

U.S. Pat. No. 5,312,415, to Palermo (also shows a method for discharging numerous coils from a single pusher by use of a guidewire which has a section capable of interconnecting with the interior of the helically wound coil).

U.S. Pat. No. 5,350,397, to Palermo et al. (shows a pusher having a throat at its distal end and a pusher through its axis. The pusher sheath will hold onto the end of an embolic coil and will then be released upon pushing the axially placed pusher wire against the member found on the proximal end of the vaso-occlusive coil).

The entirety of which are incorporated by reference.

Figure 5:
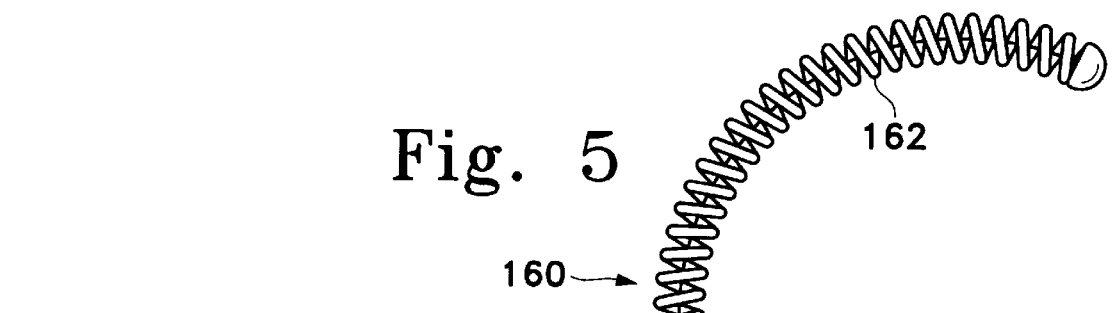
FIG. 5 shows a "C" shaped secondary shape for the inventive vaso-occlusive device.
Figure 6:
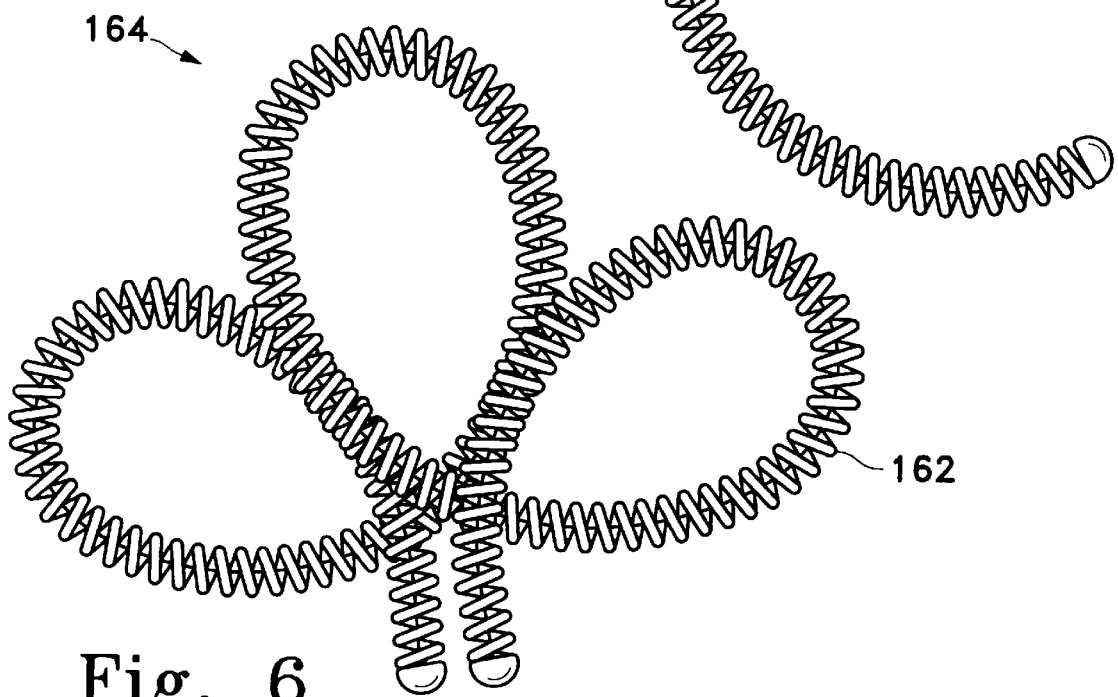
FIG. 6 shows a clover-leaf secondary shape for the inventive vaso-occlusive device.
Figure 7:
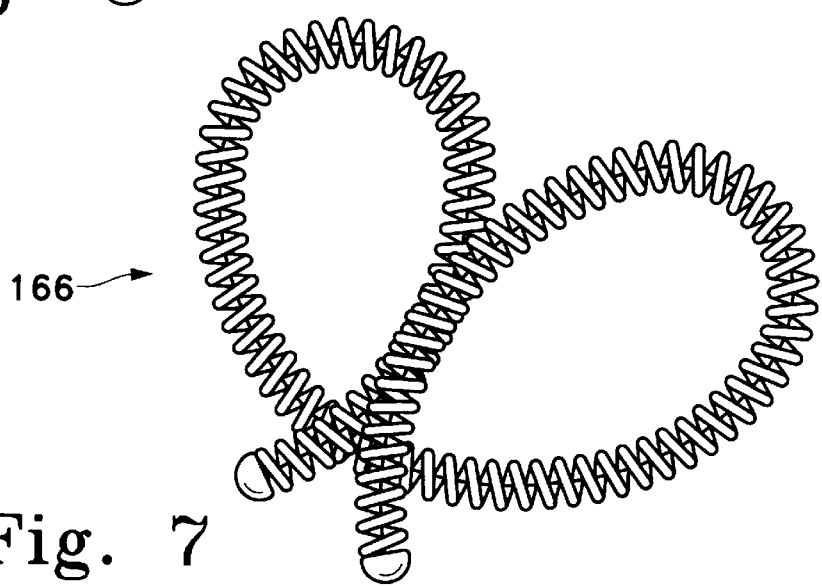
FIG. 7 shows a double-looped secondary shape for the inventive vaso-occlusive device.

As was noted above, the devices of this invention may have the simple linear shape shown in FIGS. 1 and 2 or may have shapes which are not so simple. FIGS. 5, 6, and 7 show what are termed "secondary" shapes in that they are formed from the primary coil by the simple act of winding the primary coil on a form of a desired shape and then heat treating the so-formed shape. FIG. 5 shows a "C" shaped coil assembly (160) having a stretch-resistant member (162). FIG. 6 shows a clover-leaf shaped coil assembly (164) also having a stretch-resistant member (162). FIG. 7 shows a double-loop coil assembly (166). These are indicative of the various secondary shapes suitable for this invention.

Figure 8:
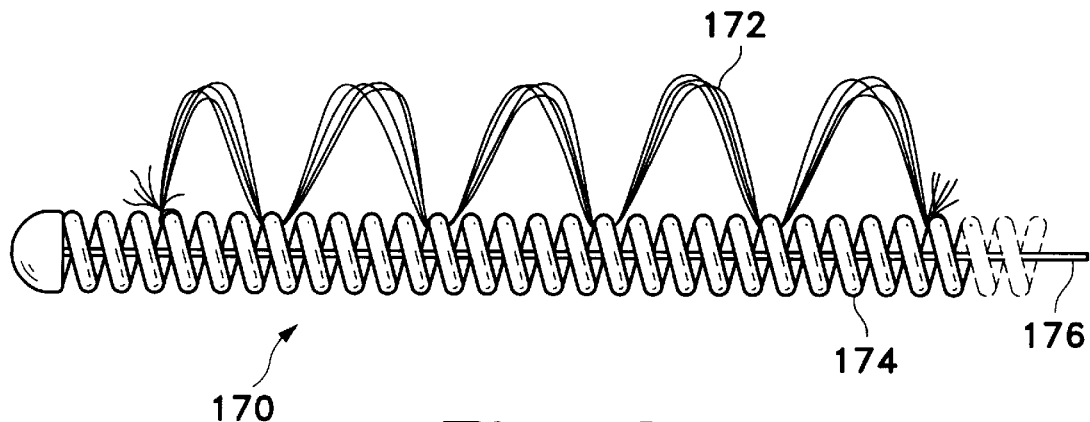
FIG. 8 shows attachment of external fibrous material to the inventive vaso-occlusive device.

Additionally, these inventive devices may also be used in conjunction with various external fiber adjuncts. FIG. 8 shows a partial side-view of a linear variation of the inventive device (170) having filamentary material (172) looping through the coil (174). This method of attachment is described in greater detail in U.S. Pat. Nos. 5,226,911 and 5,304,194, to Chee et al, the entirety of which are incorporated by reference. A further description of a desirable fiber attachment is shown in U.S. Pat. application No. 08/265,188, to Mirigian et al, filed Jun. 24, 1994.

Figure 9:
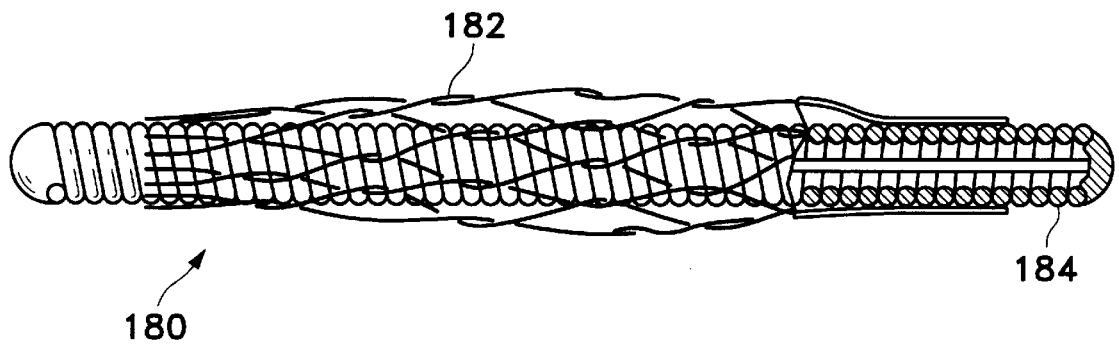
FIG. 9 shows attachment of external braided fibrous material to the inventive vaso-occlusive device.

FIG. 9 shows a partial cutaway of a device (180) having a braided covering (182) of a filamentary material and a stretch-resisting member (184). This method of enveloping a coil is described in greater detail in U.S. Pat. Nos. 5,382,259, to Phelps et al, the entirety of which is incorporated by reference.

The fibrous woven or braided tubular materials may be made from a biocompatible materials such as Dacron (polyester), polyglycolic acid, polylactic acid, fluoropolymers (polytetrafluoroethylene), Nylon (polyamide), or silk. The strands forming the braid should be reasonably heavy, e.g., having tensile strength of greater than about 0.15 pounds. The materials mentioned, to the extent that they are thermoplastics, may be melted or fused to the coils. Alternatively, they may be glued or otherwise fastened to the coils. Preferred materials are Dacron.

Figure 10A:
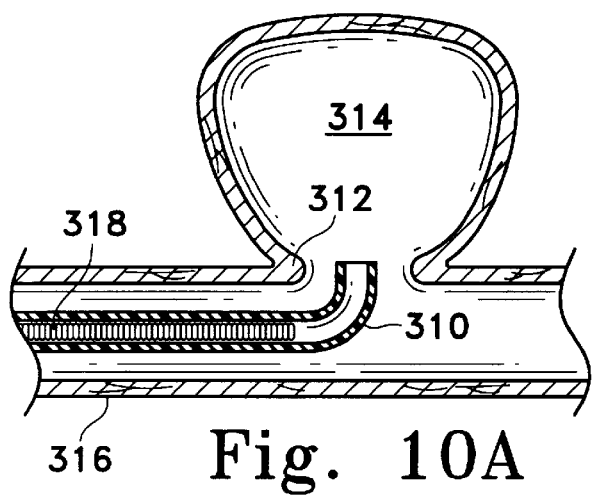
FIGS. 10A–10D show a procedure for introducing a vaso-occlusive coil such as found in the other Figures into an aneurysm.
Figure 10B:
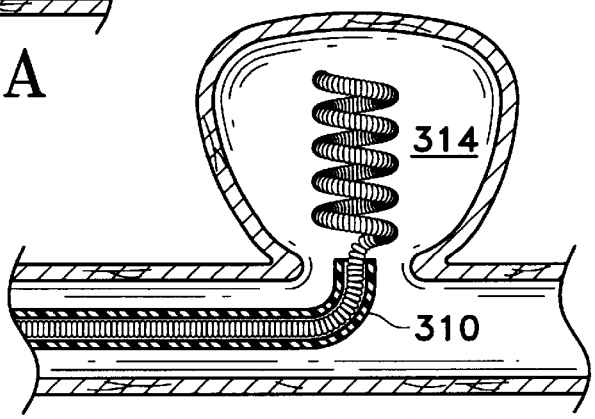
Figure 10C:
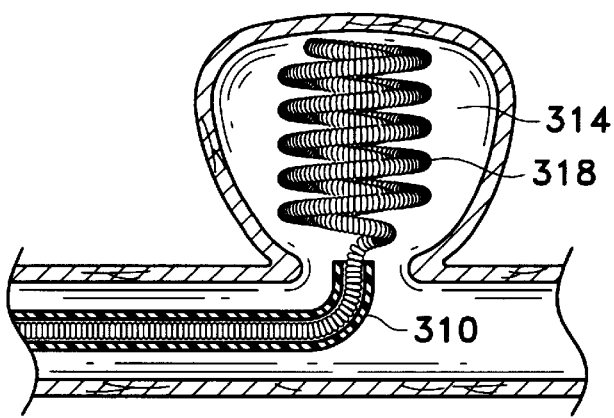
Figure 10D:
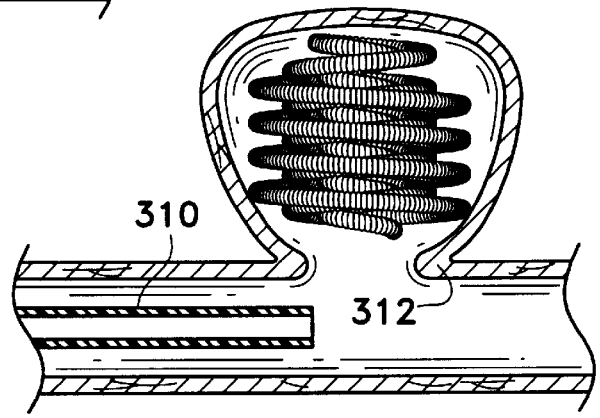

FIGS. 10A–10D depict a common deployment method for introduction of the inventive vaso-occlusive devices described here. It may be observed that these procedures are not significantly different than those described in the Ritchart et al. patent mentioned above. Specifically, FIG. 10A shows the distal tip of a delivery catheter (310) which is within the opening (312) of an aneurysm (314) found in an artery (316). The distal or end section of the vaso-occlusive device (318) is shown within the catheter (310). In FIG. 10B, the distal end portion of the vaso-occlusive device (318) has exited the distal end of the catheter (310) and has wound into a secondary shape within the aneurysm (314). FIG. 10C shows the completion of the formation of the secondary shape within the aneurysm (314). FIG. 10D shows the separation of the vaso-occlusive device (318) from the pusher, placement within the aneurysm (314), and the withdrawal of the catheter from the mouth of the aneurysm.

Once the inventive coil is in place in an aneurysm or other site, there may be an occasion during which the coil must be moved or even withdrawn. For instance, in FIG. 10D, the coil might extend through the mouth (312) of the aneurysm into the artery. Occlusion would not be desirable in the artery. A device such as the endovascular snare shown in U.S. Pat. No. 5,387,219, to Rappe, may then be used to grasp the exposed coil and move it or retrieve it from the body. The stretch-resisting member of this invention prevents the coil from stretching into a single strand of wire and multiplying in length.

Modification of the above-described variations of carrying out the invention that would be apparent to those of skill in the fields of medical device design generally, and vaso-occlusive devices specifically, are intended to be within the scope of the following claims.

We claim as our invention:

1. A vaso-occlusive device comprising:
   i. an outer helically wound primary coil having a first end, a second end, an axis between said first and second ends, and having a lumen between said first end and second end;
   ii. a stretch-resisting polymeric member extending through at least a portion of said lumen and fixedly attached to said primary coil in at least two axially separated locations; and
   iii. a deployment tip attached to at least one of said first end or said second end and said deployment tip comprises an electrolytically detachable end adapted to detach from a pusher by imposition of an electric current on said pusher.

2. The device of claim 1, wherein said polymeric stretch-resisting member comprises at least one fiber.

3. The device of claim 1, wherein said polymeric stretch-resisting member comprises multiple fibers.

4. The device of claim 1, wherein said polymeric stretch-resisting member comprises a wire.

5. The device of claim 1, wherein said polymeric stretch-resisting member comprises a helical coil.

6. The device of claim 1, wherein said outer helically wound primary coil is configured to form a secondary shape.

7. The device of claim 1, wherein said helically wound coil comprises a metal selected from the group consisting of platinum, palladium, rhodium, gold, tungsten, and their alloys.

8. The device of claim 7, wherein said helically wound coil comprises an alloy of platinum and tungsten.

9. The device of claim 1, wherein said helically wound coil comprises an alloy selected from the group consisting of stainless steels and super-elastic alloys.

10. The device of claim 9, wherein said helically wound coil comprises a nickel-titanium super-elastic alloy.

11. The device of claim 1, wherein said polymeric stretch-resisting member comprises a polymer containing a radio-opaque filler.

12. The device of claim 1, additionally comprising external filamentary material attached to said primary coil.

13. The device of claim 12, wherein the polymeric stretch-resisting member comprises a thermoplastic.

14. The device of claim 13, wherein said thermoplastic comprises polyethylene terephthalate.

15. The device of claim 13, wherein said thermoplastic also forms a cap at located on at least one end of said primary coil.

16. The device of claim 15, wherein said cap is of the same diameter as said primary coil.

17. The device of claim 15, wherein said thermoplastic forms caps at both ends of said primary coil.

18. The device of claim 1, wherein the polymeric stretch-resisting member adheres to at least one end of said primary coil.

19. The device of claim 1, wherein the polymeric stretch-resisting member extends through said lumen and is fixedly attached to at least one of said first and second ends.

20. The device of claim 1, wherein the polymeric stretch-resisting member comprises a ribbon.

21. The device of claim 20, wherein said ribbon comprises a metal selected from the group consisting of platinum, palladium, rhodium, gold, tungsten, and their alloys.

22. The device of claim 21, wherein said ribbon comprises an alloy of platinum and tungsten.

23. The device of claim 20, wherein said helically wound coil comprises an alloy selected from the group consisting of stainless steels and super-elastic alloys.

24. The device of claim 23, wherein said helically wound coil comprises a nickel-titanium super-elastic alloy.

* * * * *